United States Patent [19]

Fitton

[11] Patent Number: 4,485,091

[45] Date of Patent: Nov. 27, 1984

[54] DERMATOLOGICAL COMPOSITIONS

[75] Inventor: Harry Fitton, Oldham, England

[73] Assignee: Quinoderm Limited, Oldham, England

[21] Appl. No.: 397,416

[22] Filed: Jul. 12, 1982

Related U.S. Application Data

[63] Continuation of Ser. No. 169,494, Jul. 15, 1980, abandoned, which is a continuation-in-part of Ser. No. 2,891, Jan. 12, 1979, abandoned.

[51] Int. Cl.$^3$ ............... A61K 7/135; A61K 37/40; A61K 31/47; A61K 31/155
[52] U.S. Cl. ............... 424/62; 424/179; 424/258; 424/315; 424/317; 424/322; 424/326
[58] Field of Search ........... 424/62, 179, 258, 315, 424/317, 322, 326

[56] References Cited

U.S. PATENT DOCUMENTS

| | | | |
|---|---|---|---|
| 3,123,521 | 3/1964 | Wentworth et al. | 424/130 |
| 3,574,827 | 4/1971 | Beerbower | 424/83 |
| 3,639,574 | 2/1972 | Schmolka | 424/130 |
| 3,678,156 | 7/1972 | MacMillan et al. | 424/68 |
| 3,704,227 | 11/1972 | Hill | 424/130 |
| 3,816,324 | 6/1974 | Fine | 424/130 |
| 3,954,974 | 5/1976 | Herzog et al. | 424/170 |
| 4,041,033 | 8/1977 | Douglass | 424/65 |

FOREIGN PATENT DOCUMENTS

| | | | |
|---|---|---|---|
| 669158 | 11/1938 | Fed. Rep. of Germany | 424/62 |
| 719029 | 3/1942 | Fed. Rep. of Germany | 424/62 |
| 1520945 | 3/1968 | France | 424/168 |
| 465188 | 7/1935 | United Kingdom | 424/62 |
| 462977 | 4/1937 | United Kingdom | 424/130 |
| 466172 | 5/1937 | United Kingdom | 424/62 |
| 827331 | 2/1960 | United Kingdom | 424/130 |
| 1185684 | 3/1970 | United Kingdom | 424/62 |
| 1398258 | 6/1975 | United Kingdom | 424/130 |
| 1468815 | 3/1977 | United Kingdom | 424/168 |

OTHER PUBLICATIONS

Pharmaceutical Formulas, 1953, vol. I, pp. 88, 268, 296, 845, 862, 863 and 279.
Pharmaceutical Formulas, 1947, vol. 2, pp. 76 and 94.

*Primary Examiner*—Dale R. Ore
*Attorney, Agent, or Firm*—Fleit, Jacobson, Cohn & Price

[57] ABSTRACT

A dermatological composition in the form of a cream, lotion or gel contains hydrogen peroxide. The composition has an oil medium dispersed in an aqueous medium and the hydrogen peroxide is contained in the aqueous medium together with a buffer to maintain an acid pH.

11 Claims, No Drawings

DERMATOLOGICAL COMPOSITIONS

This application is a continuation of application Ser. No. 169,494, filed July 15, 1980, now abandoned, which in turn is a continuation-in-part of Ser. No. 002,891, filed Jan. 12, 1979, now adandoned.

This invention relates to dermatological compositions containing hydrogen peroxide. The invention is primarily concerned with such compositions for human therapeutic use. It is however to be understood that the invention is not intended to be limited to such use and thus for example compositions according to the invention may be used in a veterinary rather than a human context and/or may be of cosmetic rather than therapeutic effect.

Hydrogen peroxide has a well-known therapeutic and cosmetic effect in a dermatological context due to its ability to make available free oxygen in contact with the skin. Further, hydrogen peroxide is a readily available and relatively inexpensive substance which need only be used in small quantities for dermatological purposes due to the high proportion of available oxygen which it contains. In these respects therefore, hydrogen peroxide is a desirable substance for dermatological use. Hydrogen peroxide has not however found wide acceptance in proprietary dermatological compositions due to certain disadvantages which arise with the use of the substance, in particular due to the fact that the substance is very unstable, due to the possible damage to skin tissue which may be caused if the skin is exposed to an unduly large amount of hydrogen peroxide, and due to the fact that hydrogen peroxide has a high surface tension and therefore tends not to spread easily on the skin and make intimate contact therewith.

An object of the present invention is to provide a dermatological composition containing hydrogen peroxide with which the above mentioned disadvantages can be avoided or at least appreciably reduced.

According to the invention therefore there is provided a dermatological composition in the form of a cream preparation which comprises an oil medium dispersed in an aqueous medium and incorporates starch gel, said aqueous medium containing hydrogen peroxide and a buffer to maintain the pH of the composition at less than 7, characterised in that the composition is formed by mixing starch with oil and water components and then converting the starch to a gel in situ thereby to give a stable oil-in-water emulsion.

In accordance with a preferred embodiment of the invention, the composition is an oil-in-water cream preparation of the 'vanishing' cream kind in which a small proportion of an oil medium is dispersed as an emulsion in a high proportion of an aqueous medium. Such cream preparation when applied to the skin does not have an oily or greasy feel and is therefore particularly suitable for treating distressing skin conditions such as acne.

With the composition of the invention, due to the incorporation of the hydrogen peroxide in an oil-in-water cream preparation and due to the presence of the acid buffer it has been found possible to achieve surprisingly good dermatological activity with a relatively small proportion of hydrogen peroxide (say no greater than 3.75% by weight) whereby the possibility of damage to the skin tissue can be avoided or at least appreciably minimised, and also to achieve a remarkable stability to the extent that such dermatological activity can be expected to be retained after an appreciable period of storage. For good stability the nature and amount of buffer is preferably such as to give a pH in the range 2.5 to 6.5 and most preferably in the range 2.5 to 3.2. Further, the use of starch gel formed in situ has very important advantages with regard to the incorporation of the hydrogen peroxide and also enables easy and intimate application to the skin.

Thus, the starch gel, as formed in situ, becomes integrally incorporated in the oil-in-water emulsion and imparts properties thereto which facilitate the spreading of the composition over the surface of the skin despite the high surface tension of the hydrogen peroxide and which facilitate ready 'vanishing' of such composition despite the presence of the oil medium. These properties arise, it is believed, because droplets of the oil medium are enclosed by the starch gel which acts effectively to combine the different components of the composition to give a stable uniform blend.

A further important advantage arising from the use of the starch gel formed in situ is that the hydrogen peroxide can be added at a final stage to a cold mixture of the other components. That is, oil components aqueous components and the starch can be mixed and treated, as by heating same, to produce the starch gel and it has been found that the resulting cream mixture when cold will readily incorporate hydrogen peroxide or indeed any other aqueous substance. Usually it is difficult to incorporate aqueous substances into cream mixtures without heating, and of course hydrogen peroxide decomposes when heated. Thus, with the present invention, hydrogen peroxide can be readily incorporated in a stable composition without loss of activity.

The starch used in forming the composition of the invention may be of any suitable origin, for example, it may be maize starch, rice starch, potato starch, wheat starch.

The starch may be incorporated by adding same in the form of an aqueous slurry to a pre-formed emulsion of the water and oil components, the resulting mixture then being heated and stirred to form the gel. The emulsion may be pre-formed by adding the water component at a temperature of about 70° C. (or higher) to the oil component also at a temperature of about 70° C. (or higher) with stirring. The starch slurry may be added to such emulsion, the mixture then being further heated to 95°-100° C. with stirring and the resulting gel being allowed to cool with stirring.

The said oil component with which the starch is mixed prior to gel formation may comprise some or all of the total oil phase of the composition.

The oil medium may be of any suitable form appropriately selected such that it is dermatologically innocuous and such that is is compatible with the remaining constituents of the preparation. Thus, for example, the oil medium may comprise a saturated hydrocarbon wax and an emulsifying wax. The hydrocarbon wax may be one or more substances selected from hydrocarbons of general formula $C_nH_{2n+2}$ and fatty acids of general formula $C_nH_{2n+1}COOH$ and may comprise for example hard paraffin wax, liquid paraffin Adeps Solidus, white or yellow soft paraffin wax. Preferably, the substance known as "white soft paraffin wax" which is a semi-solid mixture of hydrocarbons obtained from petroleum and having a melting point in the range 38° C. to 56° C. is used. The emulsifying wax may be any suitable ionic or non-ionic substance. Thus for example it may be a non-ionic substance of general formula R—CH$_2$—O(CH$_2$.CH$_2$.O)$_n$H and may be for example the substance known as Lanbritol Wax N21 (Trade Mark) which is a mixture of 86% by weight cetostearyl alcohol with 14% by weight of a non-ionic emulsifier. The cetostearyl alcohol contains 30% by weight cetyl alcohol and 70% by weight stearyl alcohol and the emulsifier is a cetyl-oleyl ether of polyethylene glycol having a mean chain length of 14 ethylene oxide units. Alternatively, the substance know as Cetomacrogol Emulsifying Wax BPC may be used. This substance comprises a compound having the formula CH$_3$(CH$_2$)$_m$—O—CH$_2$(CH$_2$.OCH$_2$)$_n$CH$_2$OH where m is 15 to 17 and n is 19 to 23, and four times its weight of cetostearyl alcohol. Alternatively, an anionic emulsifying wax may be used, such as Emulsifying Wax BPC, comprising 9 parts by weight cetostearyl alcohol and one part sodium lauryl sulphate or other sodium salt of a sulphated primary aliphatic alcohol or any mixture of salts.

With regard to the buffer, as mentioned this may be such as to maintain the pH at 2.5 to 6.5 and any suitable buffer may be used for this purpose. Thus, for example, there may be used an acid such as lactic acid, citric acid, tartaric acid, maleic acid, hydroxysuccinic acid with an acid salt. Said acid salt may be any of sodium and potassium acid phosphate, sodium and potassium acid citrate, sodium and potassium acid tartrate.

In addition, if desired the composition may incorporate one or more of: a chelating agent, a pharmaceutically active quinoline derivative, chlorhexidine gluconate, urea, hydrocortisone, a corticosteroid, and other substances which provide an auxiliary therapeutic or cosmetic effect or act to improve (possibly synergistically) the therapeutic or cosmetic effect of one or more of the other constituents.

With regard to the quinoline derivative, the composition may incorporate such a derivative which is a bactericidal and keratolytic agent for example a substance selected from potassium 8-hydroxyquinoline sulphate, 8-hydroxyquinoline sulphate, iodochlorhydroxyquinoline, di-iodohydroxyquinoline and di(8-hydroxy-7-iodoquinoline-5-sulphonate).

With regard to the chelating agent, this may be provided for the purpose of minimising any loss of activity and discolouration of the quinoline derivative, where such derivative is provided, and in order to minimise any loss of available oxygen from the peroxide particularly due to the presence of metal ions in the preparation. Such chelating agent may be any suitable substance for example ethylenediamine tetra-acetic acid (EDTA) or any of the disodium, trisodium, dipotassium, and tripotassium salts of EDTA.

The starch incorporated in the preparation of the invention provides therapeutic astringent properties.

The invention will now be described further by way of example only.

EXAMPLE 1

A cream preparation is prepared by mixing the following constituents:

| | |
|---|---|
| White Soft Paraffin Wax | 9.5% by weight |
| Emulsifying Wax (e.g. Lanbritol Wax N21) | 7% by weight |
| Chelating Agent (EDTA) | 0.09% by weight |
| Sodium Acid Phosphate | 0.5% by weight |
| Lactic Acid | 0.5% by weight |
| 100% Hydrogen Peroxide | 1.5% by weight |
| Potassium 8-Hydroxyquinoline Sulphate | 0.5% by weight |

-continued

| | |
|---|---|
| Maize Starch | 5.25% by weight |
| Water | to 100% by weight |

The paraffin wax, emulsifying wax, EDTA and some of the water are introduced into the bowl of a Hobart mixer. The bowl is placed in a water bath and the contents are heated to 95° C. and stirred for a period of time (say about 60 minutes).

The sodium acid phosphate is dissolved in water (at say 50°–60° C.) and the starch is blended in with stirring to give a smooth slurry. This slurry is added to the mixture in the Hobart bowl and the temperature is brought back up to 95° C. with stirring until a gel is formed. The gel is allowed to cool to below 40° C. with further stirring.

The lactic acid and the potassium 8-hydroxyquinoline sulphate are separately dissolved in water and added to the cooled gel. The hydrogen peroxide is then blended into the contents of the Hobart bowl with stirring to give a uniform mixture.

The resulting preparation is a smooth oil-in-water 'vanishing' cream having pH 2.6. The cream can be stored in tubes or other containers which should be opaque or of limited transparency to avoid decomposition in sunlight. The cream can be applied easily and smoothly to the skin and has good dermatological activity for example in the treatment of acne whilst being cosmetically acceptable. The cream does not tend to cause damage to skin tissue or undue irritation and is stable and retains its activity even after long storage. Any decompositon of the hydrogen peroxide merely produces water and does not give rise to the formation of any possibly harmful decomposition products.

In order to demonstrate that the preparation has antibacterial activity subsequent to manufacture thereof and subsequent to storage of the preparation, the following tests were performed on a four-month old sample of the preparation.

The cream was placed in wells on plates sown with different strains of different bacterial species. After incubation of 24-72 hours presence and sizes of inhibition zones were noted. The tests were performed on nutrient agar or brain heart infusion agar and also on blood agar which breaks down hydrogen peroxide and rapidly eliminates its anti-bacterial activity.

The results were as follows:

| | Proportion of Strains Inhibited | |
|---|---|---|
| Species | Nutrient Agar or Brain Heart Infusion Agar | Blood Agar |
| Staph. aureus | 16/16 | 16/16 |
| Str. pyogenes | 6/6 | 6/6 |
| Ps. aeruginosa | 6/6 | 0/8 |
| Coliform species | 10/10 | 2/16 |
| Diphtheroid species | 8/8 | 8/8 |
| Propionobacterium acnei | 2/2 | 2/2 |
| Clostridium welchi | 2/2 | 2/2 |

The preparation gave wide zones of inhibition for all strains of all species tested using nutrient agar or brain heart infusion agar. Removal of hydrogen peroxide by the blood agar gave rise to elimination of anti-bacterial activity in respect of all Pseudomonas aeruginosa strains and most of the Coliform species strains. In the case of the other species anti-bacterial activity was retained, probably due to the presence of quinoline derivative, but the inhibition zones were reduced in size by about one-half to two-thirds.

It can be seen therefore that the preparation contains hydrogen peroxide having utilisable anti-bacterial activity despite the incorporation of the hydrogen peroxide into the cream preparation and despite the storage of the preparation.

In the Example given above, the proportion of white soft Paraffin Wax may be varied between 1% and 38%, a corresponding change being made in the proportion of water.

Additionally or alternatively, it is possible to vary the proportion of hydrogen peroxide within a range having a preferred upper limit of 3.75%. A preferred range, however, is 0.75 to 2%. The proportion of water is correspondingly changed to allow for any variation.

Additionally or alternatively, it is possible to replace the quinoline derivative with 100% Chlorhexidine Gluconate, a range having an upper limit of 2% being preferred for this constituent and 0.5% being a particularly preferred proportion. The proportion of water is correspondingly changed to allow for any variation in this respect.

Additionally or alternatively, urea can be incorporated in the composition in any desired suitable proportion, provided that the proportion of white soft Paraffin Wax and emulsifying wax is less than the proportion of water in the formulation.

It will be noted that with the embodiment described above the hydrogen peroxide can be intimately incorporated in an emulsion in the cold. Incorporation in a warm mix presents problems due to the thermal instability of hydrogen peroxide. The incorporation into an emulsion of course facilitates spreading on the skin.

It is to be understood that a composition according to the invention need not incorporate an auxiliary therapeutic agent (such as the quinoline derivative) but may comprise essentially only the hydrogen peroxide, oil medium, water, starch, and buffer as can be seen from the following example.

EXAMPLE 2

A cream preparation is prepared by mixing the following constituents:

| | |
|---|---|
| White Soft Paraffin Wax BP | 9.5% by weight |
| Emulsifying Wax (e.g. Emulgade F supplied by Henkel & Cie GmbH of Dusseldorf) | 7.0% by weight |
| Sodium Acid Phosphate | 0.5% by weight |
| Lactic Acid BP | 0.5% by weight |
| Hydrogen Peroxide BP 100% | 1.5% by weight |
| Maize Starch BP | 5.25% by weight |
| Water BP | to 100% by weight |

The resulting preparation is a smooth, white oil-in-water vanishing cream having a pH in the range of 2.5 to 3.2 and having an actual hydrogen peroxide content in the range 1.35% to 1.65%. A batch of the preparation having a pH 2.66 at 25° C. and containing 1.544% hydrogen peroxide was analysed at intervals over a period of six months and the following successive results were obtained for hydrogen peroxide content 1.454
1.425
1.422
1.376
1.398

The preparation was therefore found to have good stability.

The above-mentioned batch was applied to Standard Lawns of Bacteria and the following zones of inhibition were obtained.

| Bacteria | No. of Strains | Zone of Inhibition (mm) |
|---|---|---|
| Staph. aureus | 33 | 36.24 ± 2.07 |
| Streptococcal species | | |
| Group A Str. pyogenes | 14 | 37.25 ± 3.94 |
| Other Strep. species (Gps. A,B,C,G and non-groupable) | 26 | 35.5 ± 3.07 |
| Mixed Gram negative species (E. coli, Proteus sp., Klebsiella sp.) | 19 | 27.53 ± 2.78 |
| Pseudomonas aeruginosa | 9 | 26.55 ± 2.24 |
| Clostridium welchi | 6 | 39.2 ± 1.64 |
| Diphtheroid organism (including Prop. acnei and two anaerobic species) | 12 | 26.1 ± 8.5 |

It is of course to be understood that the invention is not intended to be restricted to the details of this example composition. Thus, for example, a composition according to the invention need not be used for the treatment of acne, it may be used for the treatment of burns or for the treatment of any other suitable human or animal skin condition or for any other suitable dermatological purpose.

Indeed, the composition of the invention is particularly suitable for treating Stasis Ulcer and other kinds of ulcers of the skin. Further, whilst reference is made herein to hydrogen peroxide proportions up to 3.75% by weight it is to be understood that the composition of the invention renders possible the stable and convenient incorporation of higher proportions up to 5% or higher.

What we claim is:

1. A method of preparing a dermatological composition in the form of a cream preparation, said composition having an oil medium dispersed in an aqueous medium, and incorporating starch gel, said aqueous medium containing hydrogen peroxide and a buffer to maintain the pH of the composition at less than 7, comprising the steps of:
   i. forming a mixture of that part of said aqueous medium not including said hydrogen peroxide, and said oil medium and starch;
   ii. stirring and heating said mixture so that said starch is converted to said starch gel in situ thereby forming a stable, smooth oil-in-water emulsion;
   iii. cooling said emulsion;
   iv. adding the remainder of said aqueous medium including said hydrogen peroxide to said cooled emulsion and stirring to give a uniform mixture.

2. The process of claim 1, wherein the composition contains up to 3.75% by weight hydrogen peroxide.

3. The process of claim 2, wherein the composition contains 0.75% to 2% by weight hydrogen peroxide.

4. The process of claim 1, 2, or 3, wherein the pH is 2.5 to 6.5.

5. The process of claim 1, 2, 3 or 4, wherein the oil medium comprises a saturated hydrocarbon wax and an emulsifying wax.

6. The process of claim 1, 2, 3, 4 or 5, wherein the buffer comprises lactic acid, citric acid, tartaric acid, maleic acid, or hydroxysuccinic acid with an acid salt.

7. The process of claim 6, wherein the acid salt is sodium or potassium acid phosphate, sodium or potassium acid citrate, or sodium or potassium acid tartrate.

8. The process of claim 1, 2, 3, 4, 5, 6 or 7, further comprising one or more of a chelating agent, a pharmaceutically active quinoline derivative, chlorhexidine gluconate, urea, hydrocortisone, or a corticosteroid.

9. The process of claim 8, wherein said quinoline derivative is potassium 8-hydroxyquinoline sulphate, 8-hydroxyquinoline sulphate, iodochlorhydroxyquinoline, di-iodohydroxyquinoline or di(8-hydroxy-7-iodoquinoline-5-sulphonate).

10. The process of claim 8 or 9, wherein said chelating agent is ethylenediamine tetra-acetic acid or the disodium, trisodium, dipotassium or tripotassium salts of said acid.

11. A dermatological composition in the form of a cream preparation prepared by the process according to claim 1.

* * * * *